(12) United States Patent
Kelly et al.

(10) Patent No.: US 7,040,319 B1
(45) Date of Patent: May 9, 2006

(54) METHOD AND APPARATUS FOR MONITORING OXYGEN PARTIAL PRESSURE IN AIR MASKS

(75) Inventors: Mark E. Kelly, League City, TX (US); Donald R. Pettit, Houston, TX (US)

(73) Assignee: The United States of America as represented by the National Aeronautics and Space Administration, Washington, DC (US)

( * ) Notice: Subject to any disclaimer, the term of this patent is extended or adjusted under 35 U.S.C. 154(b) by 64 days.

(21) Appl. No.: 10/087,866

(22) Filed: Feb. 22, 2002

(51) Int. Cl.
*A61M 16/00* (2006.01)
*A62B 7/00* (2006.01)
*F16K 31/02* (2006.01)

(52) U.S. Cl. .................... 128/204.22; 128/205.23; 128/205.25

(58) Field of Classification Search ........... 128/201.19, 128/204.22, 205.23, 202.11, 202.22, 205.22, 128/206.28, 204.23, 205.25
See application file for complete search history.

(56) References Cited

U.S. PATENT DOCUMENTS

| | | | |
|---|---|---|---|
| 2,798,588 A * | 7/1957 | Jurgens | 198/520 |
| 3,672,388 A * | 6/1972 | Ringwall et al. | 137/88 |
| 3,675,649 A * | 7/1972 | Basham et al. | 128/204.22 |
| 4,335,735 A * | 6/1982 | Cramer et al. | 137/81.1 |
| 4,373,521 A * | 2/1983 | Wattenbarger | 128/202.13 |
| 4,423,723 A * | 1/1984 | Winkler et al. | 128/202.22 |
| 4,440,166 A * | 4/1984 | Winkler et al. | 128/204.22 |
| 4,906,990 A * | 3/1990 | Robinson | 340/945 |
| 4,928,682 A * | 5/1990 | Stevenson et al. | 128/202.26 |
| 4,939,647 A * | 7/1990 | Clough et al. | 128/201.27 |
| 4,960,119 A * | 10/1990 | Hamlin | 128/204.18 |
| H1039 H * | 4/1992 | Tripp et al. | 128/206.28 |
| 5,445,160 A * | 8/1995 | Culver et al. | 600/532 |
| 5,503,145 A * | 4/1996 | Clough | 128/204.22 |
| 5,659,296 A * | 8/1997 | Debe et al. | 340/632 |
| 5,666,949 A * | 9/1997 | Debe et al. | 128/202.22 |
| 6,091,974 A * | 7/2000 | Palti | 600/345 |
| 6,165,105 A * | 12/2000 | Boutellier et al. | 482/13 |
| 6,199,550 B1 * | 3/2001 | Wiesmann et al. | 128/204.23 |
| 6,239,724 B1 * | 5/2001 | Doron et al. | 340/870.28 |
| 6,289,238 B1 * | 9/2001 | Besson et al. | 600/509 |
| 6,289,890 B1 * | 9/2001 | Bliss et al. | 128/203.11 |
| 6,401,714 B1 * | 6/2002 | Giorgini | 128/204.26 |
| 6,429,558 B1 * | 8/2002 | Hisafumi | 310/81 |

* cited by examiner

*Primary Examiner*—Glenn K. Dawson
*Assistant Examiner*—Michael Mendoza
(74) *Attorney, Agent, or Firm*—Kurt G. Hammerle; Theodore U. Ro; James M. Cate

(57) ABSTRACT

Method and apparatus are disclosed for monitoring an oxygen partial pressure in an air mask and providing a tactile warning to the user. The oxygen partial pressure in the air mask is detected using an electrochemical sensor, the output signal from which is provided to a comparator. The comparator compares the output signal with a preset reference value or range of values representing acceptable oxygen partial pressures. If the output signal is different than the reference value or outside the range of values, the air mask is vibrated by a vibrating motor to alert the user to a potentially hypoxic condition.

8 Claims, 8 Drawing Sheets

METHOD AND APPARATUS FOR MONITORING OXYGEN PARTIAL PRESSURE IN AIR MASKS

ORIGIN OF THE INVENTION

The invention described herein was made by employee(s) of the United States Government and may be manufactured or used by or for the Government of the United States of America for governmental purposes without the payment of any royalties thereon or therefor.

BACKGROUND OF THE INVENTION

1. Field of the Invention

The present invention relates generally to oxygen systems and, more particularly, to a method and apparatus for monitoring the partial pressure of oxygen in such oxygen systems.

2. Description of the Related Art

Users of oxygen masks and air masks in general are at risk of oxygen deprivation, or hypoxia, in the event of a malfunction or breakdown in the oxygen system. High-performance military aircrafts, for example, are typically pressurized according to a schedule that often results in cabin pressure altitudes above 10,000 feet. The pilots of these aircraft are required to wear oxygen masks in order to maintain a sufficient level of oxygen. However, a malfunction of the oxygen regulating system, poor fitting of the oxygen mask, or failure of the oxygen hose or distribution system can result in hypoxia. Accordingly, a number of warning devices have been developed to detect and alert the users of air masks to hypoxia inducing conditions.

Existing hypoxia warning devices, however, are typically integrated with, or are an extension of, the oxygen systems being monitored. For example, presently available hypoxia warning devices commonly share the same power source as the oxygen systems. As a result, a malfunction or breakdown in the oxygen system can often result in misleading or even false indications of the oxygen partial pressure.

In addition, existing hypoxia warning systems typically only analyze the air that is being supplied to the mask as opposed to analyzing the air directly within the mask. These systems often fail to detect loose or poor fitting oxygen masks or hose connections from the oxygen system to the mask. As a result, hypoxic conditions can and do frequently arise even though the oxygen level of the air that is being supplied is normal. Also, a failure in the aircraft pressurization system which causes the cabin pressure to slowly decrease can result in hypoxic conditions with no observed failure in the oxygen supply system.

Moreover, current hypoxia warning devices typically warn the users of a potentially hypoxic condition by sounding an alarm, illuminating a visual indicator, or a combination of both. These warning indicators, however, may not be adequate or effective when the user has already begun to experience some of the symptoms of hypoxia. For example, a warning tone or light may more easily go unnoticed or unheeded by a pilot who is already groggy, drowsy, or who has a reaction time that is slowed by the onset of hypoxia. Also, warning systems that tie into an aircraft's existing caution lights and audible tones require significant and costly modifications to every aircraft that the system is applied too.

Accordingly, it is desirable to be able to provide an improved hypoxia warning device that is independent of the oxygen system being monitored, monitors the air directly within the air mask, requires minimal or no modifications to existing airplane cockpits or emergency cabin depressurization systems, and is also sufficiently annoying, irritating, and aggravating to provoke the user into taking prompt and immediate corrective actions.

SUMMARY OF THE INVENTION

The present invention provides a method and apparatus for monitoring an oxygen partial pressure directly within an air mask and providing a tactile warning to the user wherein little or no modifications to existing airplane cockpits or emergency cabin depressurization systems are required. The oxygen partial pressure directly within the air mask is detected using an oxygen partial pressure sensor, the output signal from which is provided to a comparator. The comparator compares the output signal with a preset reference value or a range of values representing an acceptable oxygen partial pressure. If the output signal is different than the reference value or outside the range of values, the air mask is vibrated by a vibrating motor to alert the user to a potentially hypoxic condition.

In general, in one aspect, the invention is directed to an apparatus for monitoring an oxygen partial pressure in an air mask of an oxygen system. The system comprises a sensor mounted in the air mask and capable of providing an output signal corresponding to the oxygen partial pressure in the air mask. A comparator is connected to the sensor and configured to compare the output signal with a reference signal corresponding to a desired oxygen partial pressure. A power source independent of the oxygen system being monitored is connected to the sensor and the comparator. A vibrator is connected to the comparator and configured to vibrate if the generated signal is determined to be lower than the reference signal.

In general, in another aspect, the invention is directed to a method of monitoring an oxygen partial pressure in an air mask of an oxygen system. The method comprises generating a signal corresponding to the oxygen partial pressure in the air mask, the signal generated independently of the oxygen system. The method further comprises comparing the generated signal with a reference signal corresponding to a desired oxygen partial pressure and vibrating the air mask if the generated signal is determined to be lower than the reference signal.

In general, in still another aspect, the invention is directed to a device for monitoring an oxygen partial pressure in an air mask of an oxygen system. The device comprises means for generating a signal corresponding to the oxygen partial pressure in the air mask, means for comparing the generated signal with a reference signal corresponding to a desired oxygen partial pressure, and means for powering the generating means and the comparing means independently of the oxygen system. The device further comprises means for vibrating the air mask if the generated signal is determined to be lower than the reference signal.

In general, in yet another aspect, the invention is directed to an apparatus for monitoring an oxygen partial pressure in an oxygen mask of an oxygen system of an aircraft. The apparatus comprises a sensor mounted in the air mask and capable of providing an output signal corresponding to the oxygen partial pressure in the air mask, a comparator connected to the sensor and configured to compare the output signal with a reference signal corresponding to a desired oxygen partial pressure, and an amplifier connected to the sensor and the comparator and configured to amplify the output signal. The apparatus further comprises a power source connected to the sensor and the comparator and derived from a communications cord of the aircraft, and a vibrating motor connected to the comparator and attached to a surface of the air mask, the vibrating motor configured to vibrate if the generated signal is determined to be lower than the reference signal. An alarm is connected to the comparator and configured to activate if the generated signal is determined to be lower than the reference signal, and a switch allows a user to selectively disconnect the power source.

In general, in yet another aspect, the invention is directed to a method of monitoring an oxygen partial pressure in an air mask of an oxygen system. The method comprises generating a signal corresponding to the oxygen partial pressure in the air mask, the signal generated independently of the oxygen system. The method further comprises comparing the generated signal with a reference signal corresponding to a desired oxygen partial pressure, and activating an alarm connected to the air mask if the generated signal is determined to be outside a predefined reference range.

In general, in yet another aspect, the invention is directed to an apparatus for monitoring an oxygen partial pressure in an air mask of an oxygen system. The apparatus comprises a sensor mounted in the air mask and capable of providing an output signal corresponding to the oxygen partial pressure in the air mask, a comparator connected to the sensor and configured to compare the output signal with a reference signal corresponding to a desired oxygen partial pressure, and a power source connected to the sensor and the comparator, the power source being independent of the oxygen system. The apparatus further comprises an alarm connected to the comparator and configured to actuate if the generated signal is determined to be outside a predefined reference range.

BRIEF DESCRIPTION OF THE DRAWINGS

A more complete understanding of the invention may be had by reference to the detailed description herein when taken in conjunction with the accompanying drawings, wherein.

DETAILED DESCRIPTION OF THE DRAWINGS

Figure 1:
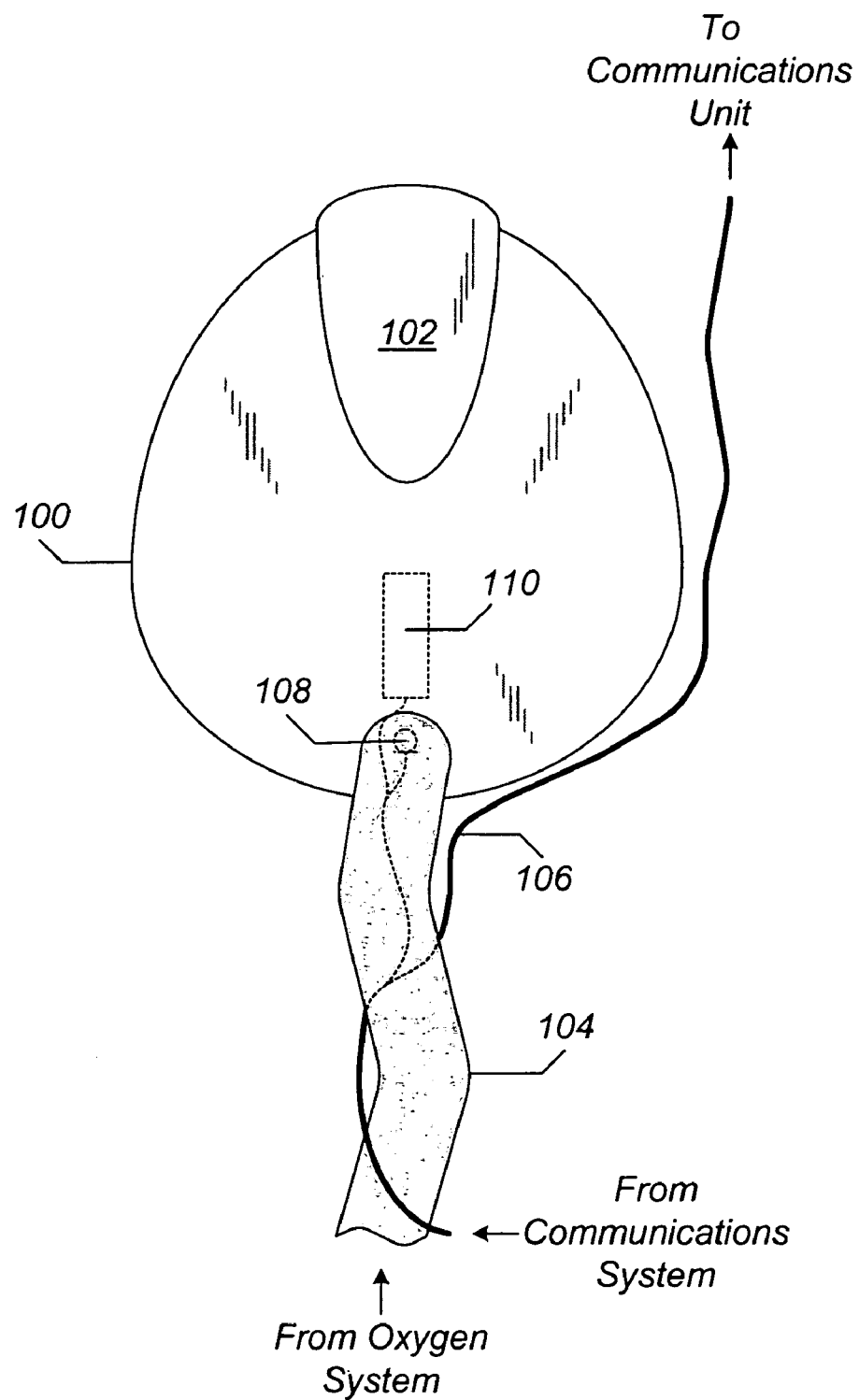
FIG. 1 illustrates a frontal view of an air mask according to some embodiments of the invention; embodiments of the invention.

Following is a detailed description of the drawings wherein reference numerals for the same and similar elements are carried forward.

Embodiments of the invention provide a method and apparatus for monitoring oxygen partial pressure in an air mask of an oxygen system. In some embodiments, an oxygen partial pressure sensor is used to detect the oxygen partial pressure of the air flow from the oxygen system into the air mask. The oxygen partial pressure sensor generates an output signal that corresponds to the partial pressure of the oxygen in the air mask. The output signal from the oxygen partial pressure sensor is subsequently compared to a reference signal representing an acceptable oxygen partial pressure. If the output signal is determined to be different (e.g., lower) than the reference value or outside a predefined range of values, then the comparator causes a vibrator to vibrate the air mask, thereby alerting the user to a potentially hypoxic condition. Power for the oxygen partial pressure sensor and the comparator is provided from a power source independent of the oxygen system.

The partial pressure of oxygen in the air mask is monitored as opposed to the concentration of oxygen because the former quantity is subject to changes due to fluctuations in the total pressure. As an aircraft increases and decreases in altitude, changes in the cabin pressure affect the total pressure significantly and, therefore, the partial pressure of oxygen can also change significantly. Changes in the concentration of oxygen are also common, however, in aircrafts with diluter-regulators that mix air with oxygen as a function of altitude.

Additionally, hypoxia is known to be more related to the oxygen partial pressure than to the concentration of oxygen. Thus, even if the total pressure and/or the concentration of oxygen changes, as long as the oxygen partial pressure is maintained above a certain predefined minimum, hypoxia may be avoided. Equation (1) describes the relationship between the total pressure $P_T$ in the air mask, the concentration of oxygen $Y_{O2}$ in the air mask, and the oxygen partial pressure $P_{O2}$ in the air mask:

$$P_{O2} = Y_{O2} \cdot P_T \quad (1)$$

As can be seen, the oxygen partial pressure $P_{O2}$ is the product of the total pressure $P_T$ and the concentration of oxygen $Y_{O2}$. Thus, measuring the oxygen partial pressure $P_{O2}$, as opposed to measuring the concentration of oxygen $Y_{O2}$, can simplify the sensor design because the total pressure $P_T$ is not required to be measured, as would be the case for a sensor that measures only concentration.

Referring now to FIG. 1, an air mask 100 according to some embodiments of the invention is shown. The air mask 100 may be of the kind used by a pilot in an aircraft cockpit oxygen system, or it may be of the kind used by airline crew members in an emergency cabin depressurization system. Included with the air mask 100 is a nose piece 102 that fits over a user's nose in order to effect a comfortable, but snug fit. An air hose 104 is connected to the air mask 100 and extends from an oxygen system (not expressly shown) that provides oxygen to the user. A communications cord 106 extends from the aircraft communications system along the air hose 104 and around the air mask 100 to the communications unit (not expressly shown). Mounted within the air mask 100 are a microphone 108 and a hypoxia warning device 110 according to some embodiments of the invention, both of which are shown here in dotted lines.

Figure 2:
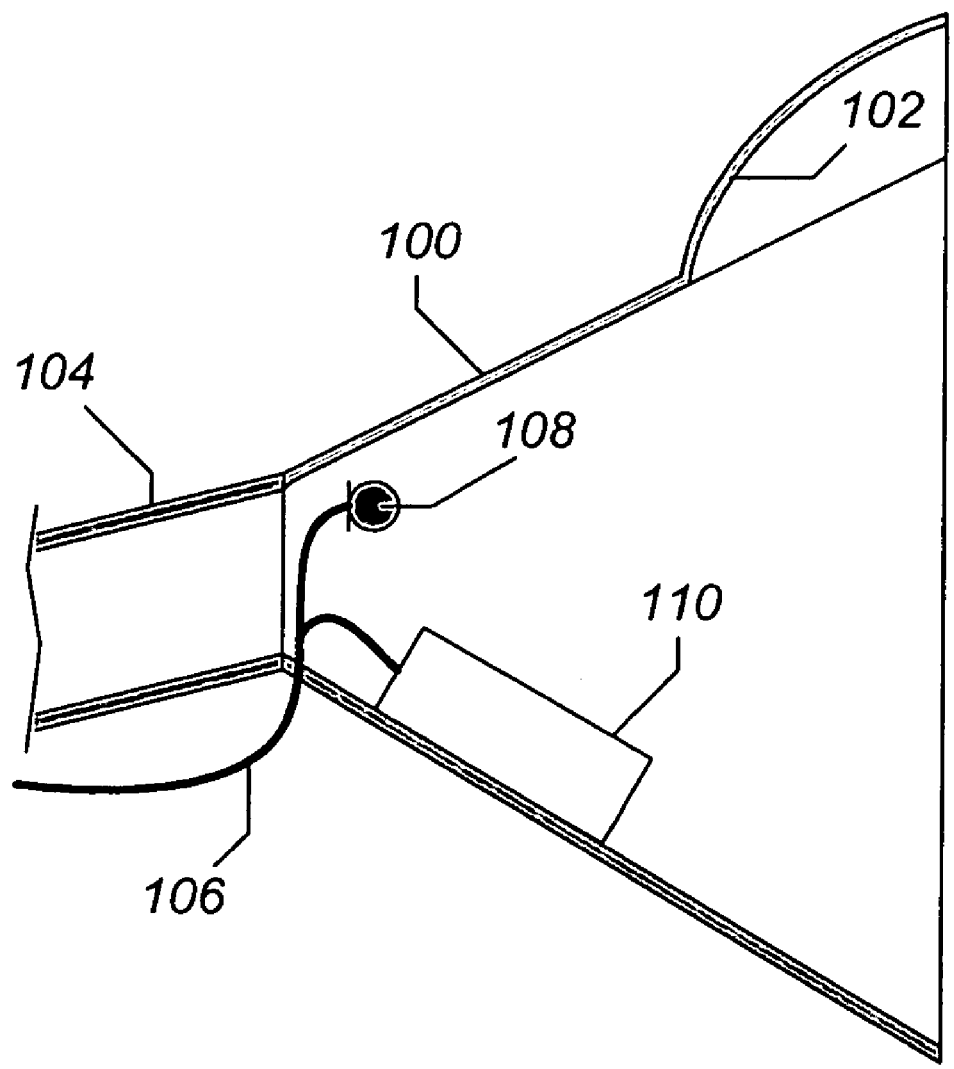

A cross-sectional side view of the air mask 100 is shown in FIG. 2, where it can be seen that the hypoxia warning device 110 is attached or otherwise mounted to an inner surface of the air mask 100. Part of the communications cord 106 extends into the air mask 100 to connect the microphone 108 to the communications systems. This routing of the communications cord 106 into the air mask 100 provides power for the microphone 108 and is standard for most aircraft. In accordance with some embodiments of the invention, the communications cord 106 is also used to provide power to the hypoxia warning device 110. Thus, the hypoxia warning device 110 can be connected to, and can draw power from, the same communications cord 106 that connects the microphone 108 to the communications system. This arrangement provides a convenient and easy to install power source for the hypoxia warning device 110, and allows the hypoxia warning device 110 to operate independently of the oxygen system.

In operation, the hypoxia warning device 110 is configured to detect and monitor the oxygen partial pressure directly within the air mask 100. By measuring the atmosphere directly within the air mask, the hypoxia warning device 110 can detect malfunctions such as a leak in the air hose connecting the oxygen system and the air mask 100. If the oxygen partial pressure falls below a certain acceptable level, the hypoxia warning device 110 is configured to activate a vibrator that vibrates the air mask 100, or portions thereof, to warn the user that a potentially hypoxic condition exists. It has been found that such a tactile warning on the nose or face of the user can be more effective than, for example, a visual or audio warning alone for alerting a user who may already be groggy, drowsy, or who may otherwise have a delayed response time due to the onset of hypoxia. More specifically, the vibrating sensation of the air mask 100 across the user's nose and face can irritate, aggravate, or otherwise provoke a possibly hypoxic user into prompt and immediate corrective actions. In addition, the vibrator can create sufficient mechanical vibration to break the microphone VOX and produce a very loud and distinct whining tone over the aircraft audio system. This tone alerts other users, if present in a multi-crew aircraft, that a crew member is having oxygen partial pressure problems so the crew can work together to solve the problem.

Figure 3:
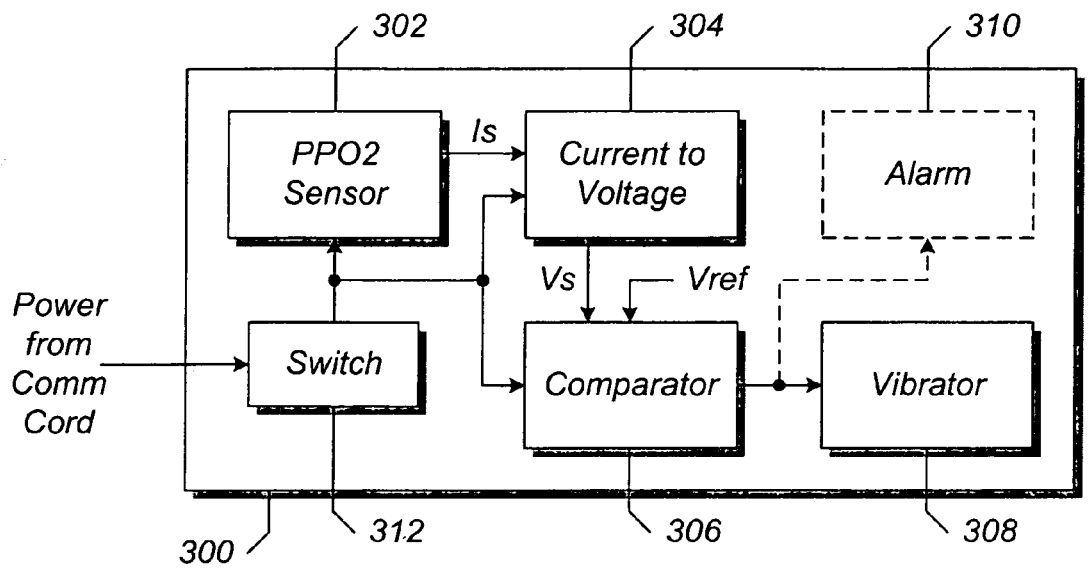
FIG. 3 illustrates a functional block diagram of an oxygen partial pressure monitoring apparatus according to some embodiments of the invention.

Referring now to FIG. 3, a block diagram of a hypoxia warning device 300 according to some embodiments of the invention is shown. The hypoxia warning device 300 includes an oxygen partial pressure sensor 302 (PPO2), a current-to-voltage converter 304, a comparator unit 306, a vibrator 308, and optionally, an audio or visual alarm 310 (in dashed lines), all interconnected as shown.

The oxygen partial pressure sensor 302, which may be a zirconium or a lead based electrochemical sensor, is capable of detecting the partial pressure of the oxygen in the air mask and generating an output signal that is proportional to the detected oxygen partial pressure. Such a sensor is known in the electrochemical art and may be obtained from, for example, Thermo Gas Tech, Newark, Calif. Electrochemical sensors have about a year and a half of working life, so the circuitry of the hypoxia warning device 110 should be designed to allow for replacement of the sensor. Furthermore, these sensors should be protected from liquid or water that might enter from condensation of water vapor from breathing. Many of these sensors have a built-in semi-permeable membrane that prevents liquid water from entering the sensor. Such a membrane should be provided externally to the sensor if one is not built-in. The response time of the oxygen partial pressure sensor 302 is typically on the order of 10 seconds, which is desirable for some embodiments of the invention in order to avoid picking up minor fluctuations in the oxygen partial pressure and fluctuations due to breathing.

The output signal of the oxygen partial pressure sensor 302, in some embodiments, may be an electric current Is which is received by the current-to-voltage converter 304. The current-to-voltage converter 304 is configured to convert the electric current Is into a corresponding voltage Vs. In some embodiments, the converter 304 is also configured to amplify the output voltage Vs by a predetermined factor or gain in order to provide a stronger voltage signal for stability during further processing.

The voltage Vs is then provided to the comparator 306, which is configured to compare the voltage Vs to a reference voltage Vref. If the output voltage Vs is about the same or higher than the reference voltage Vref, indicating normal oxygen partial pressure levels, then the output of the comparator 306 remains off. However, if the output voltage Vs falls below the reference voltage Vref, indicating potentially hypoxic conditions, then the output of the comparator 306 turns on to drive or activate the vibrator 308.

The reference voltage Vref is preferably set to correspond to an acceptable or desired oxygen partial pressure. For example, the normal oxygen partial pressure is about 0.20 atmospheres at sea level. To avoid hypoxia, it is recommended that the oxygen partial pressure be maintained at or above 80% of the normal value. Accordingly, the reference voltage Vref may be set to a value that corresponds to an oxygen partial pressure of about 0.16 atmospheres. However, depending on the application, other values for the reference voltage Vref may certainly be used as needed. For example, it is acceptable to fly without supplemental oxygen up to a cabin pressure equal to 10,000 feet. Thus, the low oxygen partial pressure alarm set point may be chosen to correspond to an elevation of 11,000 feet. At 11,000 feet, the total pressure is 0.67 atmospheres (as determined from the standard atmosphere tables in the CRC Handbook of Physics), which gives 67% of the oxygen partial pressure that one receives at sea level. The reference voltage Vref may then be set to a value corresponding to an oxygen partial pressure of 0.13 atmospheres.

Alternatively, instead of a certain value, the reference voltage Vref may be set to a predefined range of values corresponding to a desired range of oxygen partial pressures. The desired range of oxygen partial pressure may be, for example, 0.20 atmospheres to some predefined upper or lower limit. Under this arrangement, the output of the comparator 306 can be configured to remain off as long as the output voltage signal Vs stays within the predefined range of values, and to turn on only when the output voltage signal Vs falls outside the predefined range of values.

The vibrator 308 is configured to vibrate the air mask in order to warn the user of a potentially hypoxic condition. In some embodiments, the vibrator 308 may be a simple vibrating motor such as the kind found in a common pager. Such motors typically rotate an eccentric mass about a central axis at a speed of about 8,000 to 10,000 RPM. In a preferred embodiment, the vibrator 308 generates sufficient mechanical vibrations to break the microphone VOX and produce a loud audible tone as well as the vibrations that provoke the user. Power to the vibrator 308 is provided by the output of the comparator 306 that turns the vibrator 308 ON or OFF as needed.

Although a tactile warning is superior to an audio or visual warning as explained above, in some embodiments, the tactile warning may be combined with a warning tone as provided by the alarm 310. In these embodiments, the same comparator output that drives the vibrator 308 can be used to activate the alarm 310 to thereby produce a warning sound or tone. Such a warning sound or tone may be used together with the tactile warning of the vibrator 308 to increase the effectiveness of the hypoxia warning device 300.

Power for the hypoxia warning device 300, as mentioned above, may be derived by tapping into the power lines of the existing communications cord 106 (see FIGS. 1 and 2). A switch 312 connects the power lines from the communications cord to the hypoxia warning device and specifically to the oxygen partial pressure sensor 302, the current-to-voltage converter 304, and the comparator 306. Note that the types of sensors given as examples herein do not need a separate power source, but in general, sensors do require a power source. The switch 312 is preferably a locking power switch that is configured to allow a user to selectively connect and disconnect the power to the hypoxia warning device 300. The locking power switch requires a deliberate action from the user to power off the hypoxia warning device, thus preventing an inadvertent shutdown of the warning device. Such a switch 312 gives the user the ability to cut the power to the hypoxia warning device 300 in the event of a malfunction in order to turn off the vibrator 308 and/or alarm 310.

Figure 4:
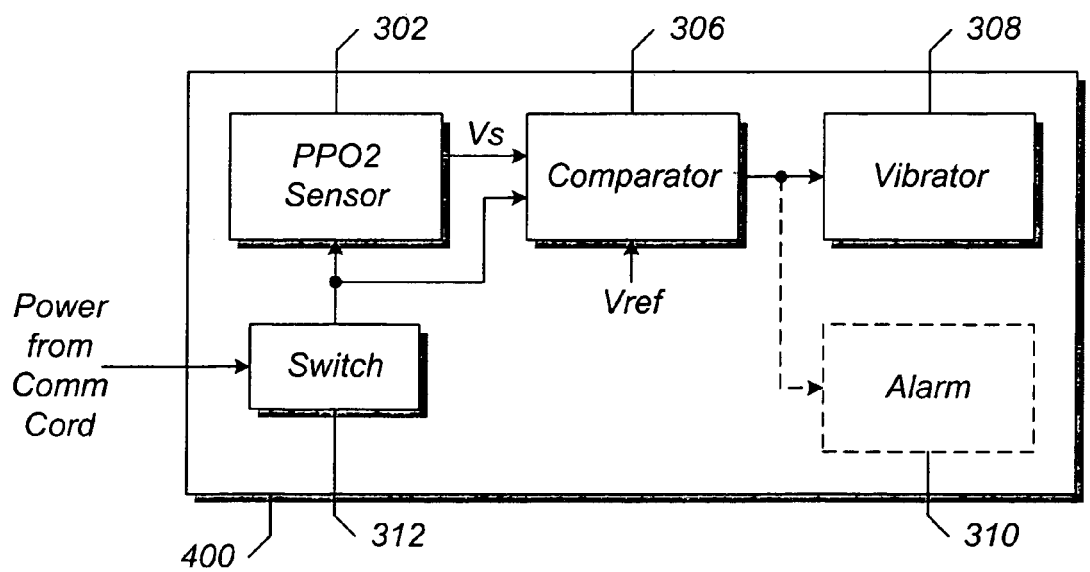
FIG. 4 illustrates a functional block diagram of another oxygen partial pressure monitoring apparatus according to some embodiments of the invention.

FIG. 4 illustrates another embodiment of the hypoxia warning device. The hypoxia warning device 400 of FIG. 4 is similar to the hypoxia warning device 300 of FIG. 3, with the exception that the oxygen partial pressure sensor 302 outputs a voltage instead of a current. Thus, the current-to-voltage converter 304 is not needed in this embodiment, and the output voltage Vs may be provided directly from the oxygen partial pressure sensor 302 to the comparator 306.

Figure 5:
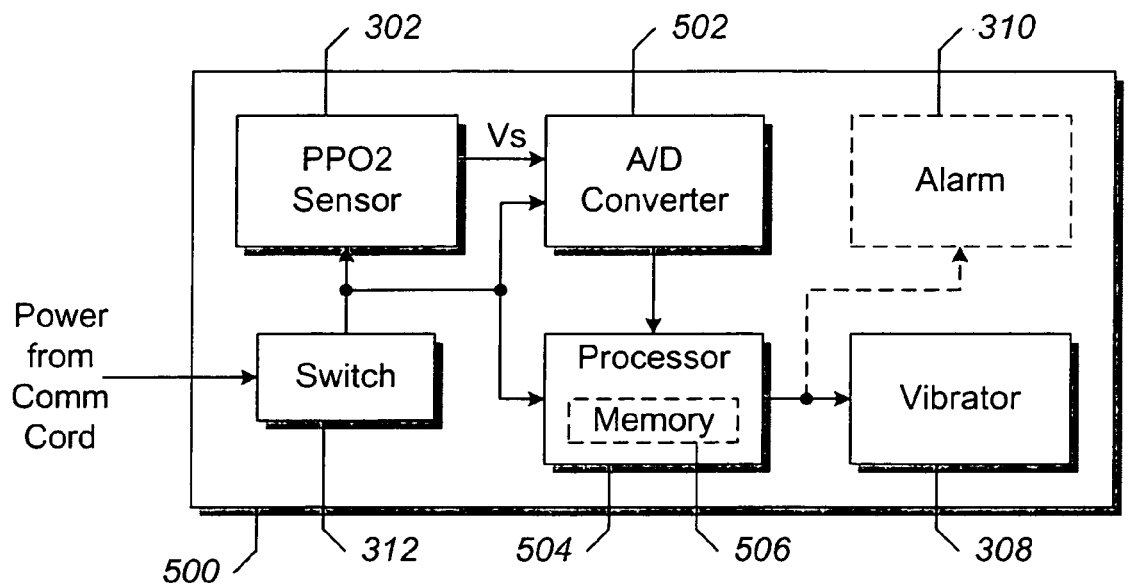
FIG. 5 illustrates a functional block diagram of yet another oxygen partial pressure monitoring apparatus according to some embodiments of the invention.

Yet another embodiment of the hypoxia warning device is illustrated in FIG. 5, where the hypoxia warning device 500 includes an analog-to-digital converter 502 connected to a processor unit 504. The analog-to-digital converter 502 is capable of converting the analog output voltage Vs from the oxygen partial pressure sensor 302 into a digital output signal. Such a digitized output signal may include any number of bits such as 8, 16, 32, or more bits depending on the resolution required by the particular application. The processor unit 504 is configured to subsequently receive and compare the digitized output signal to a reference voltage. A memory unit 506 such as a register within the processor unit 504 stores a digital reference voltage representing a desired oxygen partial pressure. If the digitized output signal is lower than the stored digital reference voltage, then the processor activates the vibrator 308 and/or the alarm 310 accordingly.

Figure 6:
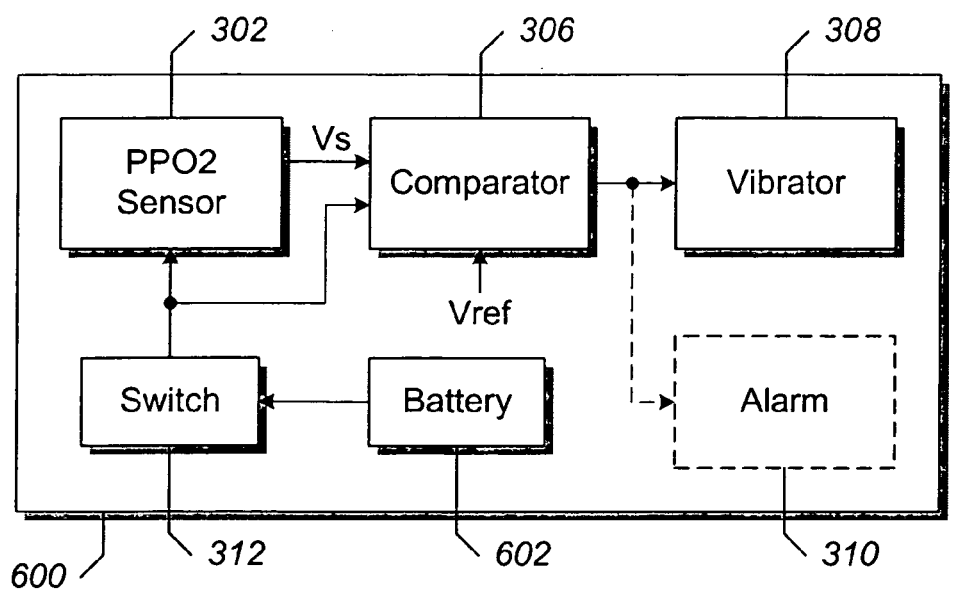
FIG. 6 illustrates a functional block diagram of still another oxygen partial pressure monitoring apparatus according to some embodiments of the invention.

Still another embodiment of the hypoxia warning device is illustrated in FIG. 6. The hypoxia warning device 600 in this embodiment is similar to the hypoxia warning device in FIG. 4, with the exception that an internal power supply 602 is included in the form of battery unit. Thus, reliance upon an external power source such as the communications cord is not needed as the hypoxia warning device in this embodiment is substantially self-contained.

Figure 7:
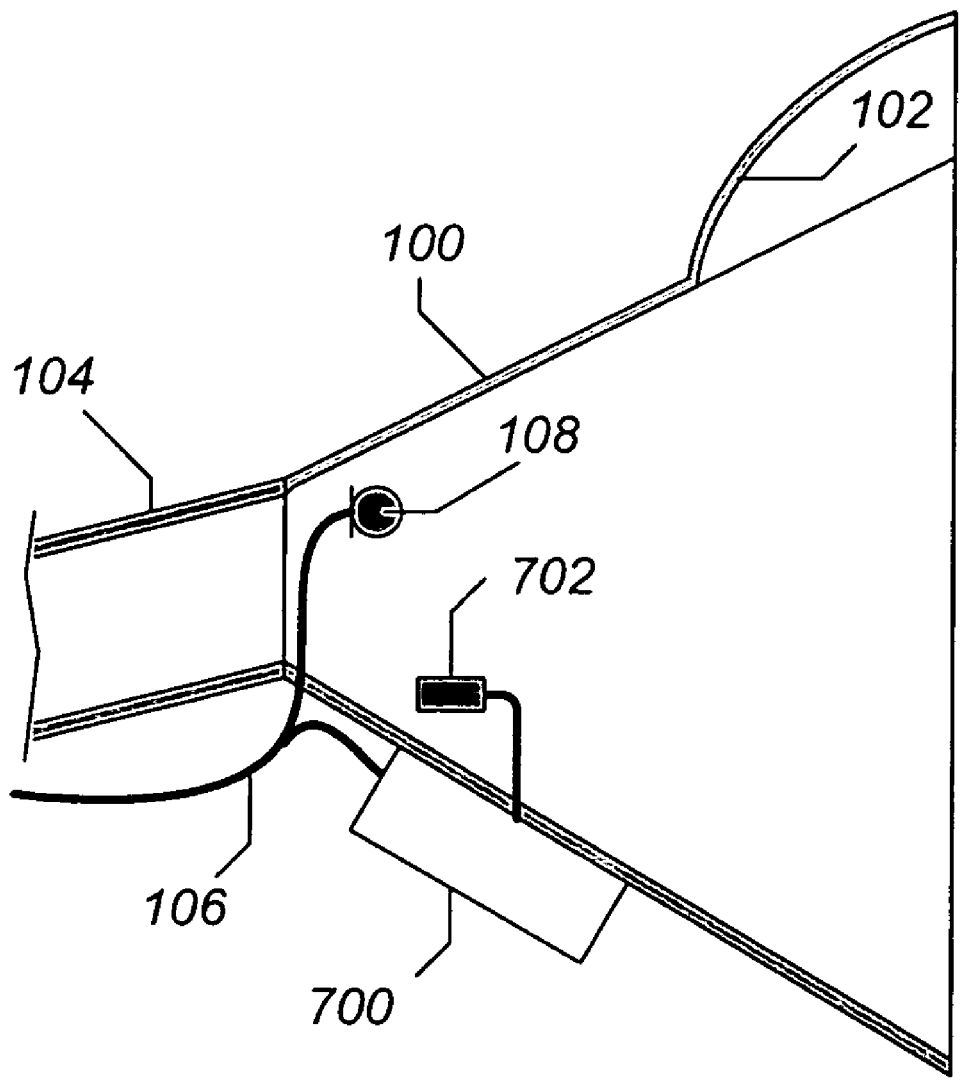
FIG. 7 illustrates another cross-sectional side view of the air mask according to some embodiments of the invention.

While the foregoing embodiments of the hypoxia warning device have been described with respect to a number of functional components, the invention is not to be limited thereto. Those of ordinary skill in the art will recognize that components may be added, removed, or modified as needed in any of the foregoing embodiments depending on the particular application. For example, referring to FIG. 7, in some embodiments, the hypoxia warning device 700 is mounted to an external surface of the air mask 100 instead of on the inside surface. These embodiments are otherwise similar to the embodiments of FIG. 2 except that only the oxygen partial pressure sensor 702 has been isolated from the hypoxia warning device 700 and is mounted inside the air mask. Such an arrangement has an advantage in embodiments where available space inside the air mask may be limited. Also, safety with the enriched oxygen often found inside the air mask may be better maintained by these embodiments. Other arrangements and combinations may also be used, such as mounting only the vibrator to the outer surface of the air mask.

In some embodiments, an amplifier having a predetermined gain may be added to any of the embodiments to boost the output signal from oxygen partial pressure sensor. Likewise, the battery unit 602 may added or removed from any of the embodiments. Moreover, some functional components may be combined with other functional components, or divided into smaller individual components. It is also possible to have an oxygen partial pressure sensor with an output inversely proportional to the partial pressure of oxygen. In such cases, the comparator should trigger the vibrator and/or alarm when the output voltage Vs rises above a preset reference value.

Figure 8:
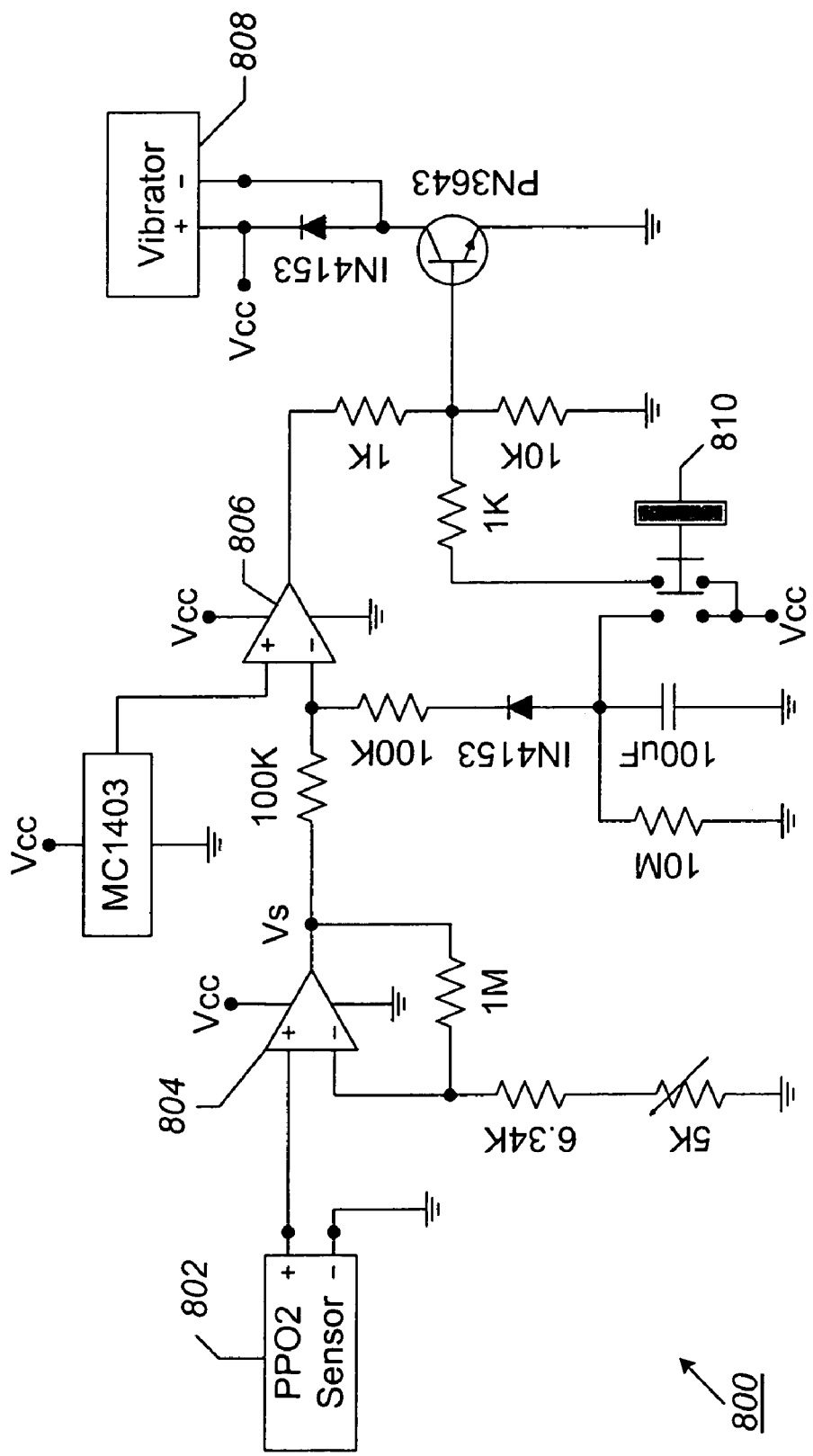
FIG. 8 illustrates a circuit diagram of an oxygen partial pressure monitoring apparatus according to some embodiments of the invention.

In some embodiments, instead of functional blocks, the hypoxia warning device may be implemented using discrete circuit components such as resistors, capacitors, diodes, one or more logic gates, and the like, or using one or more semiconductor integrated circuits such as a microprocessor, DSP, ASIC, and the like. Following is a description of one exemplary implementation of a hypoxia warning device, as shown in FIG. 8.

Figure 10:
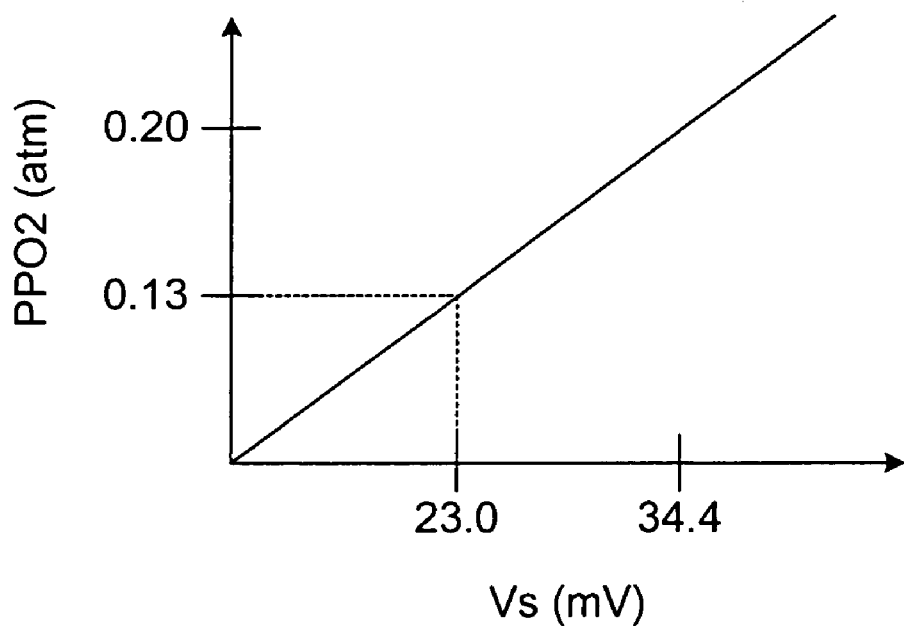
FIG. 10 is a graph of oxygen partial pressure versus output voltage of an oxygen partial pressure sensor.

A hypoxia warning device 800 in this implementation includes an oxygen partial pressure sensor 802 which is an electrochemical battery with an output voltage that is substantially linear with the oxygen partial pressure. As mentioned above, using a sensor 802 that measures oxygen partial pressure is preferred to one that measures only concentration because it is the oxygen partial pressure (which is the product of the concentration and total pressure) that is important for detecting hypoxic conditions. The particular oxygen partial pressure sensor 802 used in this implementation is model 165-0002 (available from Thermo Gas Tech, Newark, Calif.) that outputs 34.4 mV at 0.20 atmospheres of oxygen partial pressure and 23.0 mV at 0.13 atmospheres. A graph of the output voltage versus the oxygen partial pressure is shown in FIG. 10 for this model, which also has a 10 second time response so any sudden changes in oxygen partial pressure are damped. This sensor also has a built-in water barrier membrane and a working life of approximately 1.5 years.

The output voltage of the oxygen partial pressure is then provided to the positive input of the first op-amp 804 in a dual op-amp package such as a Motorola LM358 op-amp (available from Mouser Electronics, Mansfield, Tex.) with a non-inverting adjustable gain of about 100. The first op-amp 804 is used here as an amplifier, the gain for which can be adjusted as needed by adjusting the 5K trim pot to boost the output signal from the oxygen partial pressure sensor. By adjusting the gain, and hence, the output signal, a specific low oxygen partial pressure may be selected, below which a warning is issued according to various embodiments of the invention, indicating that a potentially hypoxic condition exists.

The output Vs from the first op-amp 804 is provide to a summing node and into the negative input of the second op-amp 806, which is used here as an open loop comparator. A reference voltage of 2.500 volts (+/−0.025 volts) is generated by reference voltage generator such as a Motorola MC1403 (available from Mouser Electronics, Mansfield, Tex.) and provided to the positive terminal of the second op-amp 806. The output of the second op-amp 806 stays at a few millivolts so long as the amplified sensor voltage Vs from the first op-amp 804 stays at or above 2.500 volts. When the amplified sensor voltage Vs drops below 2.500 volts (indicating a decrease in oxygen partial pressure), the output of the second op-amp quickly swings to near the supply voltage Vcc. This drives the base terminal of a PN3643 NPN switching transistor (available from Mouser Electronics, Mansfield, Tex.), which switches on the power to the vibrator.

The vibrator 808 in this implementation is a simple 1.3 volts DC pager motor. A diode such as an IN4153 diode (available from Mouser Electronics, Mansfield, Tex.) across the vibrator 808 protects the switching transistor from possible transient inductive voltage spikes from an inductive motor load.

A momentary double-pull double-throw (DPDT) push button switch 810 is used to perform two functions. First, if the motor state is not ON for low oxygen partial pressure, depressing the push button 810 triggers the switching transistor as a circuit test to demonstrate that the vibrator has power and that vibrations can be felt. Second, if the oxygen partial pressure causes the vibrator to turn ON, cycling the push button 810 resets the vibrator 810 to the OFF state for a time determined by the RC time constant of the 10 M resistor and the 100 uF capacitor (about 30 seconds).

Figure 9:
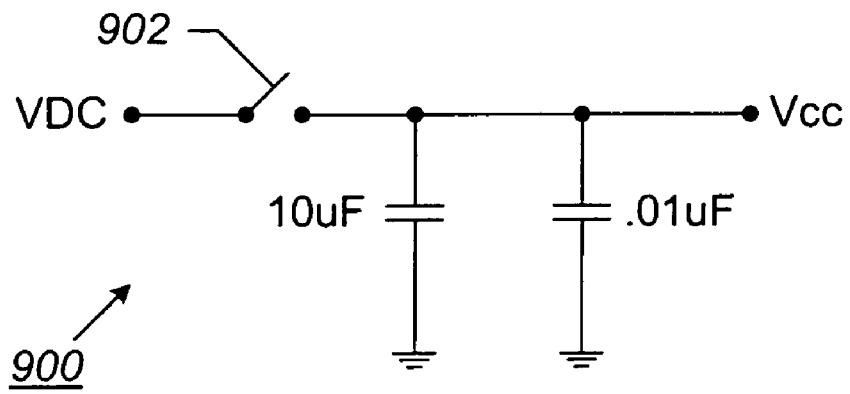
FIG. 9 illustrates a power switch for the oxygen partial pressure monitoring apparatus according to some embodiments of the invention.

Referring now to FIG. 9, a power supply circuit 900 provides power Vcc to the hypoxia warning device, which power Vcc can range from +4 to +16 volts with little effect on the circuit operation. In this embodiment, the power Vcc is derived from the same source as the microphone power and is about +6.8 volts DC. Two capacitors off of the power supply help to filter out low and high frequency noise that may be present in the power supply. A locking power switch 902 is provided so the user can disconnect the power from the circuit in the event of a system failure that erroneously switches on the vibrator.

Throughout FIGS. 8 and 9, the choice of circuit components should be made so that the circuit is stable (e.g., stable op-amp gain) through fairly large temperature swings (e.g., about −10 to +45 degrees Celsius). It is important to create an integrated design of the hypoxia warning device and the mask so that safety with the enriched oxygen often found within the mask is maintained. Material components on the inside of the mask should be oxygen compatible. Some components, for example, the vibrator motor, are preferably mounted on the external mask surface. As an additional precaution, the vibrator may be potted with oxygen compatible, fire retardant resin.

Figure 11:
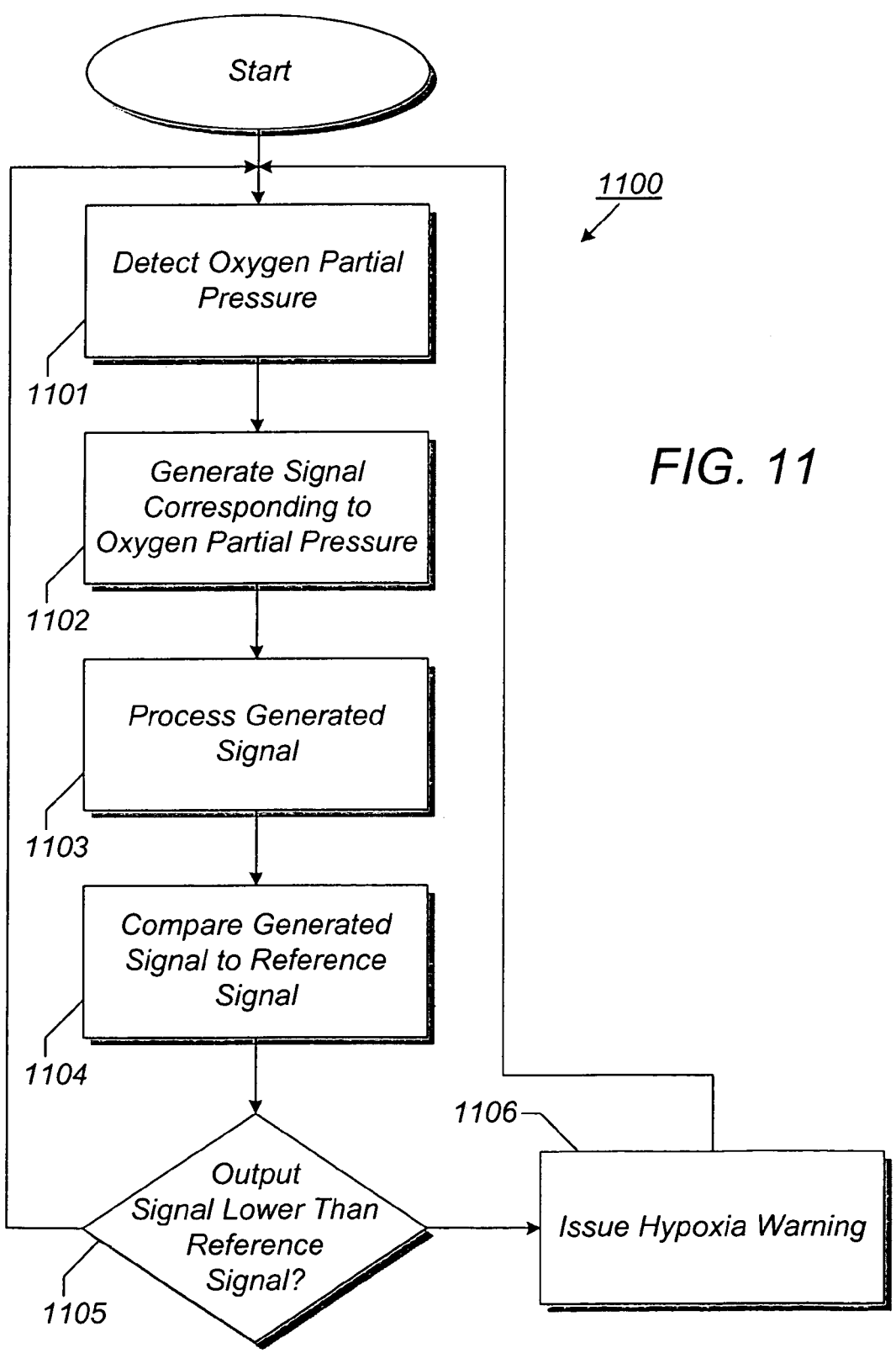
FIG. 11 is a flow chart illustrating a method of monitoring oxygen partial pressure according to some embodiments of the invention.

FIG. 11 is a flow chart of an exemplary method 1100 for monitoring oxygen partial pressure in an air mask of an oxygen system according to some embodiments of the invention. As can be seen, at step 1101, the oxygen partial pressure is detected in the air mask. At step 1102, a signal is generated that corresponds to oxygen partial pressure in the air mask. The generated signal is then processed at step 1103 including amplification, current-to-voltage conversion, and/or analog-to-digital conversion as needed. At step 1104, the processed generated signal is compared to a predefined reference signal corresponding to a desired or acceptable oxygen partial pressure. A comparison is made at step 1105 as to whether the processed generated signal is different (e.g., lower) than the reference signal or outside a predefined reference range. If yes, a warning is issued by a vibrating the air mask (via a vibrating motor) at step 1106 to alert the user of a potentially hypoxic condition. If no, the method returns to step 1101 to continue the monitoring process.

As demonstrated above, embodiments of the invention provide a method and apparatus for monitoring oxygen partial pressure in an air mask of an oxygen system. Advantages of the invention include a simple hypoxia warning device that has no connections to the oxygen system. Such a device is independent of the cockpit or cabin depressurization system of any aircraft and can thus be used with little or no aircraft modification. Also, a vibrator beating the nose and face of the user is a very effective warning for an already groggy user in an environment that is saturated with visual cues and sounds. Other advantages of the invention are readily recognized by those having ordinary skill in the art from the foregoing description and the drawings.

While a limited number of embodiments of the invention have been described, these embodiments are not intended to limit the scope of the invention as otherwise described and claimed herein. Variations and modifications from the described embodiments exist. For example, although the invention has been described with respect to an aircraft application, any application that requires supplemental oxygen, such as firefighting, mountain climbing, and the like, may make use of the invention. Furthermore, all numerical values disclosed herein are approximate values whether or not that term was used to describe the numerical values. Accordingly, the appended claims are intended to cover all such variations and modifications as falling within the scope of the invention.

What is claimed is:

1. An apparatus for monitoring an oxygen partial pressure in an air mask adapted to deliver oxygen from an oxygen system to an operator, the air mask having an interior surface, the apparatus comprising:
    a sensor positioned within the air mask, mounted on the interior surface of the air mask, and capable of providing an output signal corresponding to the oxygen partial pressure within the air mask;
    a comparator connected to the sensor and configured to compare the output signal with a reference signal corresponding to a desired oxygen partial pressure;
    a power source connected to the sensor and the comparator; and
    a vibrating motor having a rotatable, eccentric mass, mounted within the air mask, connected to the comparator, and attached to the interior surface of the air mask, the vibrating motor comprising means for vibrating the air mask if the output signal is determined to be lower than the reference signal, for generating a tactile warning on the face of the operator to alert the operator of a potentially hypoxic condition,
    wherein the apparatus is independent of the oxygen system and the apparatus does not regulate the oxygen from the oxygen system, and
    wherein the apparatus operates in a cockpit of an aircraft.

2. The apparatus of claim 1, wherein the air mask is associated with a radio audio system of the aircraft having a VOX capability and a microphone positioned within the air mask, wherein:
    the vibrating motor comprises means having sufficient mechanical vibration to break the VOX capability through the microphone and produce a warning tone through the radio audio system.

3. The apparatus of claim 1, wherein the comparator and power source are mounted within the air mask.

4. An apparatus for monitoring an oxygen partial pressure in an air mask adapted to deliver oxygen from an oxygen system to an operator, the air mask having an interior surface, the apparatus comprising:
   a sensor positioned within the air mask and capable of providing an output signal corresponding to the oxygen partial pressure within the air mask;
   a comparator connected to the sensor and configured to compare the output signal with a reference signal corresponding to a desired oxygen partial pressure;
   a power source connected to the sensor and the comparator; and
   tactile warning means, connected to the comparator, mounted within the air mask and connected to the interior surface of the air mask, for vibrating the air mask, if the output signal is determined to be lower than the reference signal, with sufficient force to generate a tactile warning on the face of the operator to alert the operator of a potentially hypoxic condition,
   wherein the apparatus is independent of the oxygen system and the apparatus does not regulate the oxygen from the oxygen system, and
wherein the apparatus operates in a cockpit of an aircraft.

5. The apparatus of claim 4, wherein the comparator and power source are mounted within the air mask.

6. A method of monitoring an oxygen partial pressure in an air mask adapted to be worn by an operator in an airplane cockpit, wherein oxygen is supplied to the air mask from an oxygen system, comprising:
   generating a signal corresponding to the oxygen partial pressure in the air mask, the signal generated independently of the oxygen system, and wherein the signal is not used to regulate the oxygen system;
   comparing the generated signal with a reference signal corresponding to a desired oxygen partial pressure;
   providing a vibrator having a rotatable eccentric element, the vibrator being connected within the air mask; and
   vibrating the air mask by activating the vibrator in contact with the mask to alert the operator of a potentially hypoxic condition if the generated signal is determined to be lower than the reference signal.

7. An apparatus for monitoring an oxygen partial pressure in an oxygen mask of an aircraft, comprising:
   a sensor positioned within the air mask and capable of providing an output signal corresponding to the oxygen partial pressure in the air mask;
   a comparator connected to the sensor and configured to compare the output signal with a reference signal corresponding to a desired oxygen partial pressure;
   an amplifier connected to the sensor and the comparator and configured to amplify the output signal;
   a power source connected to the sensor and the comparator; and
   a vibrating motor connected to the comparator and attached to the interior surface of the air mask, the vibrating motor configured to vibrate if the generated signal is determined to be lower than the reference signal, the vibrating motor comprising means for vibrating the air mask to generate a tactile warning on the face or an operator sufficient to alert the operator when in a hypoxic condition,
   wherein the apparatus is independent of the oxygen system and the apparatus does not regulate the oxygen from the oxygen system, and
   wherein the apparatus operates in a cockpit of the aircraft.

8. An apparatus for monitoring oxygen partial pressure in an air mask adapted to supply oxygen to a user aboard an aircraft, comprising:
   a sensor positioned within the air mask and capable of providing an output signal corresponding to the oxygen partial pressure directly within the air mask;
   a comparator connected to the sensor and configured to compare the output signal with a reference signal corresponding to a desired oxygen partial pressure;
   a power source connected to the sensor and the comparator; and
   a vibrator, connected to the comparator and positioned within the air mask, configured to vibrate if the generated signal is determined to be lower than the reference signal, the vibrator comprising means for providing a tactile warning on the face of an operator sufficient to alert the operator when in a hypoxic condition,
      wherein the apparatus is independent or the oxygen system,
      wherein the apparatus does not regulate the oxygen from the oxygen system, and wherein the apparatus operates in a cockpit of the aircraft.

* * * * *